(12) United States Patent
Maheshwari et al.

(10) Patent No.: US 11,936,521 B2
(45) Date of Patent: *Mar. 19, 2024

(54) IN-MEMORY WORKFLOW MANAGEMENT IN EDGE DEVICES

(71) Applicant: Oracle International Corporation, Redwood Shores, CA (US)

(72) Inventors: Prachi Maheshwari, Seattle, WA (US); Igors Sajenko, Cumming, GA (US); David Dale Becker, Seattle, WA (US); Maxim Baturin, Sammamish, WA (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/296,348

(22) Filed: Apr. 5, 2023

(65) Prior Publication Data
US 2023/0283517 A1 Sep. 7, 2023

Related U.S. Application Data

(63) Continuation of application No. 17/531,566, filed on Nov. 19, 2021, now Pat. No. 11,683,220.
(Continued)

(51) Int. Cl.
*G06F 12/00* (2006.01)
*G06F 3/06* (2006.01)
(Continued)

(52) U.S. Cl.
CPC ........ *H04L 41/0806* (2013.01); *G06F 3/0604* (2013.01); *G06F 3/0622* (2013.01);
(Continued)

(58) Field of Classification Search
CPC ..... G06F 3/0604; G06F 3/0655; G06F 3/0622
See application file for complete search history.

(56) References Cited

U.S. PATENT DOCUMENTS 8,613,070 B1 12/2013 Borzycki et al.
10,404,613 B1 9/2019 Brooker et al.
(Continued)

OTHER PUBLICATIONS

U.S. Appl. No. 17/565,337, Notice of Allowance dated May 11, 2023, 11 pages.

*Primary Examiner* — John A Lane
(74) *Attorney, Agent, or Firm* — Kilpatrick Towsend & Stockton LLP

(57) ABSTRACT

Techniques discussed herein relate to providing in-memory workflow management at an edge device (e.g., a computing device distinct from and operating remotely with respect to a data center). The edge device can operate as a computing node in a computing cluster of edge devices and implement a hosting environment (e.g., a distributed data plane). A work request can be obtained by an in-memory workflow manager of the edge device. The work request may include an intended state of a data plane resource (e.g., a computing cluster, a virtual machine, etc.). The in-memory workflow manager can determine the work request has not commenced and initialize an in-memory execution thread to execute orchestration tasks to configure a data plane of the computing cluster according to the intended state. Current state data corresponding to the configured data plane may be provided to the user device and eventually displayed.

20 Claims, 11 Drawing Sheets

Related U.S. Application Data

(60) Provisional application No. 63/173,244, filed on Apr. 9, 2021.

(51) Int. Cl.

| | |
|---|---|
| G06F 8/61 | (2018.01) |
| G06F 8/658 | (2018.01) |
| G06F 9/4401 | (2018.01) |
| G06F 9/455 | (2018.01) |
| G06F 9/50 | (2006.01) |
| G06F 11/14 | (2006.01) |
| H04L 9/08 | (2006.01) |
| H04L 9/40 | (2022.01) |
| H04L 12/46 | (2006.01) |
| H04L 41/0806 | (2022.01) |
| H04L 67/10 | (2022.01) |

(52) U.S. Cl.
CPC .......... *G06F 3/0655* (2013.01); *G06F 3/0659* (2013.01); *G06F 3/067* (2013.01); *G06F 3/0679* (2013.01); *G06F 8/61* (2013.01); *G06F 8/658* (2018.02); *G06F 9/4406* (2013.01); *G06F 9/45558* (2013.01); *G06F 9/505* (2013.01); *G06F 9/5055* (2013.01); *G06F 9/5077* (2013.01); *G06F 9/5088* (2013.01); *G06F 11/1451* (2013.01); *G06F 11/1469* (2013.01); *H04L 9/0897* (2013.01); *H04L 12/4641* (2013.01); *H04L 63/0471* (2013.01); *H04L 63/0478* (2013.01); *H04L 63/0485* (2013.01); *H04L 63/06* (2013.01); *H04L 63/0876* (2013.01); *H04L 63/162* (2013.01); *H04L 63/20* (2013.01); *H04L 67/10* (2013.01); *G06F 2009/45562* (2013.01); *G06F 2009/45587* (2013.01); *G06F 2009/45595* (2013.01); *G06F 2201/84* (2013.01)

(56) References Cited

U.S. PATENT DOCUMENTS

| | | |
|---|---|---|
| 11,683,220 B2 | 6/2023 | Maheshwari et al. |
| 2013/0332927 A1 | 12/2013 | Tang et al. |
| 2018/0103088 A1 | 4/2018 | Blainey et al. |
| 2019/0007339 A1 | 1/2019 | Bao et al. |
| 2019/0036687 A1 | 1/2019 | Raza et al. |
| 2023/0011628 A1 | 1/2023 | Hurley et al. |
| 2023/0049501 A1 | 2/2023 | Xu et al. |

IN-MEMORY WORKFLOW MANAGEMENT IN EDGE DEVICES

CROSS-REFERENCE TO RELATED APPLICATIONS

This non-provisional application is a continuation of U.S. patent application Ser. No. 17/531,566, filed on Nov. 19, 2021, entitled "In-Memory Workflow Management in Edge Devices," and claims priority to U.S. patent application No. 63/173,244, filed on Apr. 9, 2021, entitled "Cloud Computing Edge Computing Device (Rover)," the disclosures of which are herein incorporated by reference in their entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components. For example, a centralized workflow manager may be suboptimal for managing workflows at geographically remote devices.

BRIEF SUMMARY

Techniques are provided (e.g., a method, a system, non-transitory computer-readable medium storing code or instructions executable by one or more processors) for providing in-memory workflow management at a cloud infrastructure edge computing device (e.g., a computing device configured to deliver computing and storage at remote locations separate from the centralized data center and lacking a public/private network connection). Various embodiments are described herein, including methods, systems, non-transitory computer-readable storage media storing programs, code, or instructions executable by one or more processors, and the like.

One embodiment is directed to a method for providing in-memory workflow management at an edge computing device. The method may comprise implementing a plurality of respective hosting environments within a computing cluster comprising a plurality of edge computing devices. In some embodiments, the plurality of edge computing devices implement a distributed control plane for managing respective data planes of the plurality of edge computing devices. The method may further comprise obtaining, by an in-memory workflow manager of the distributed control plane, a work request comprising a request identifier and intended state data corresponding to a respective data plane of a particular cloud-computing edge device of the plurality of edge computing devices. The method may further comprise determining, using the request identifier, that the work request has yet to be started. The method may further comprise initializing, by the in-memory workflow manager, an in-memory execution thread to execute one or more orchestration tasks associated with configuring the respective data plane according to the intended state data. The method may further comprise obtaining current state data indicating a current state of the respective data plane of the particular cloud-computing edge device. The method may further comprise providing an indication of the current state of the respective data plane.

In some embodiments, the work request is initiated by from a user device configured to communicate with one cloud-computing edge device of the plurality of edge computing devices. The in-memory workflow manager and the in-memory execution thread, in some embodiments, execute within a Docker container on the particular cloud-computing edge device.

In some embodiments, the one or more orchestration tasks associated with configuring the respective data plane according to the intended state data are executed in response to: 1) obtaining, from a distributed data store accessible to the plurality of edge computing devices, previously-received actual state data associated with the respective data plane of the particular cloud-computing edge device, 2) comparing the previously-received actual state data and the intended state data, and 3) determining that there is a difference between the previously-received actual state data and the intended state data obtained from the distributed data store.

In some embodiments, identifying that the work request has yet to be started comprises determining that a record associated with the request identifier is not yet stored in a distributed data store (e.g., in a portion of the distributed data store configured to store request identifiers of requests that have already been started) accessible to the plurality of edge computing devices.

The plurality of edge computing devices may be communicatively coupled with one another via a substrate network that is different from a public network. In some embodiments, the in-memory workflow manager, executing on the particular cloud-computing edge device, identifies the one or more orchestration tasks associated with configuring the respective data plane according to the intended state data.

In some embodiments, an edge computing device is disclosed. The edge computing device may operate as part of a computing cluster of a plurality of edge computing devices. In some embodiments, the edge computing device comprises one or more processors and one or more (non-transitory) memories configured with computer-executable instructions that, when executed by the one or more processors, cause the edge computing device to perform operations. These operations may comprise implementing a hosting environment within the computing cluster. In some embodiments, the plurality of edge computing devices implement a distributed control plane for managing respective data planes of the plurality of edge computing devices. The operations may further comprise obtaining, by an in-memory workflow manager of the edge computing device, a work request comprising a request identifier and intended state data corresponding to a respective data plane of a particular cloud-computing edge device of the plurality of edge computing devices. The operations may further comprise determining, using the request identifier, that the work request has yet to be started. The operations may further comprise initializing, by the in-memory workflow manager, an in-memory execution thread to execute one or more orchestration tasks associated with configuring the respective data plane according to the intended state data. The operations may further comprise obtaining current state data indicating a current state of the respective data plane of the particular cloud-computing edge device. The operations may further comprise providing an indication of the current state of the respective data plane.

Some embodiments disclose a non-transitory computer-readable storage medium comprising computer-executable instructions that, when executed with one or more processors of an edge computing device (e.g., an edge computing device operating as part of a computing cluster of edge computing devices, cause the edge computing device to perform the method disclosed above.

DETAILED DESCRIPTION

Figure 1:
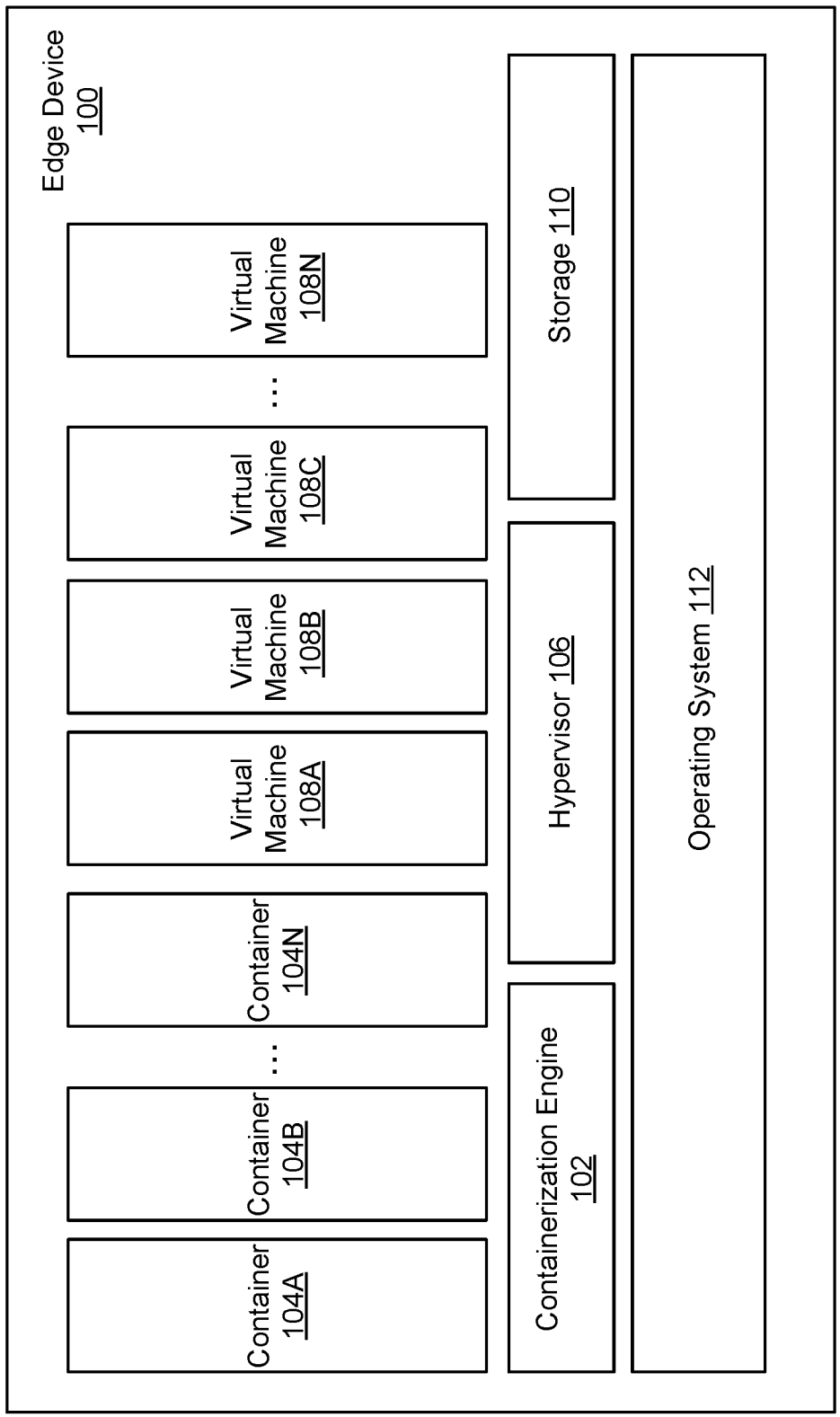
FIG. 1 is a block diagram of an example high-level architecture for a cloud infrastructure edge computing device, according to at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

INTRODUCTION

In some examples, a cloud-integrated edge service (e.g., implemented in an edge computing device) may be integral in addressing the desire to run time-sensitive cloud infrastructure application outside of a centralized data center (e.g., a datacenter of a cloud infrastructure service provider). Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud-computing edge device," a "cloud infrastructure edge computing device," or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to container(s) 104A, 104B, 104C, to 104N, collectively referred to as "container(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing or otherwise blocking direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) (e.g., a virtual machine managed by a virtualization module in the Linux kernel that allows the kernel to function as a hypervisor) and/or a hardware-based Virtual Machine (e.g., a virtual machine managed by a virtualizer, such as Quick EMUlator (QEMU), that can perform hardware virtualization to enable virtual machines to emulate of number of hardware architectures). Although storage 110 is represented as a separate component from the service(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
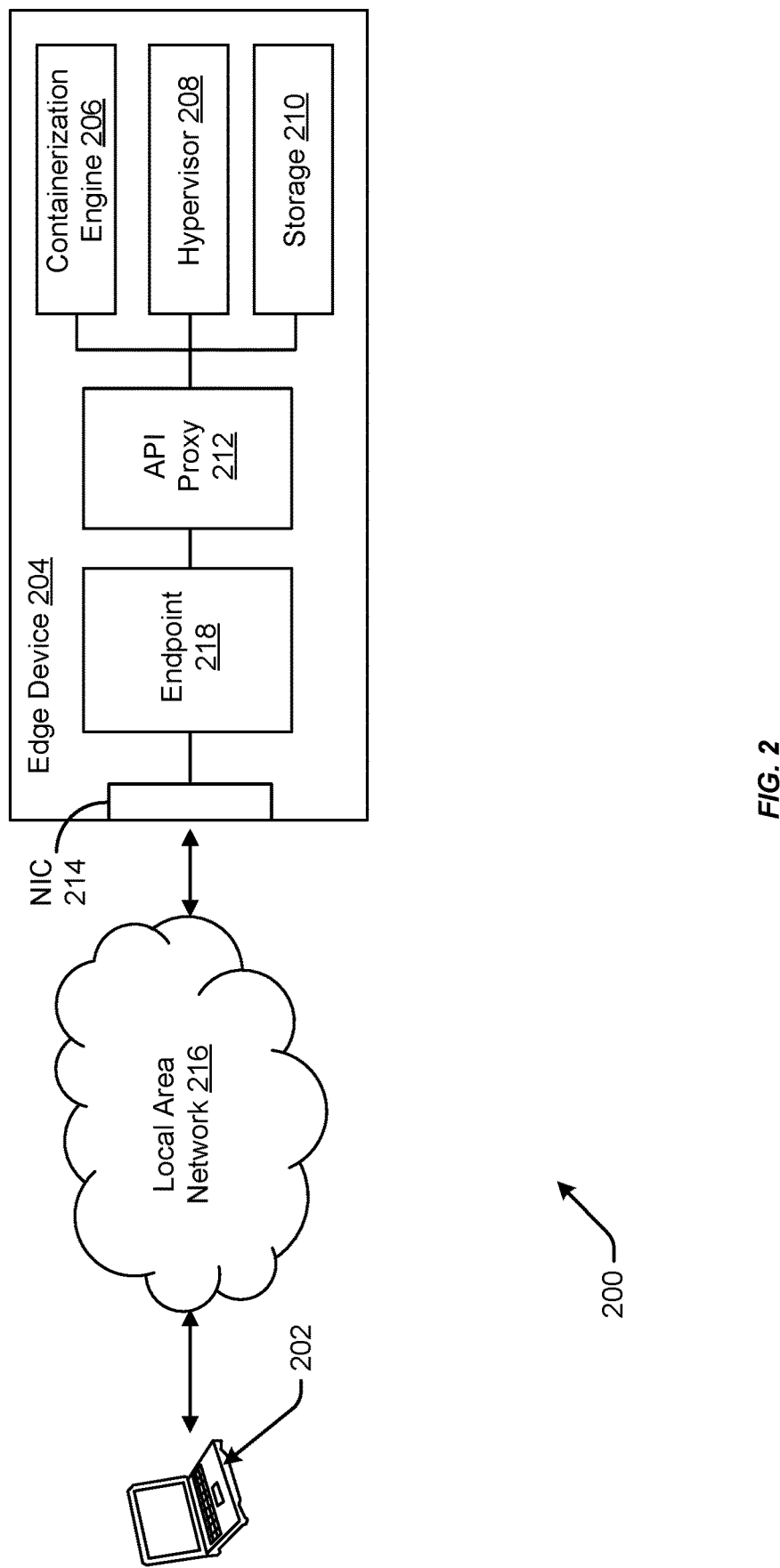
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of 1), and storage 210 (an example of the storage 110 of 1).

Additionally, as mentioned briefly above, the edge device 100 may include an API proxy 212 for managing the RESTful API calls received from the computing device 202. The API calls may enter the edge device 204 via network interface card (NIC) 214 that is internal to the edge device 204. The NIC 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
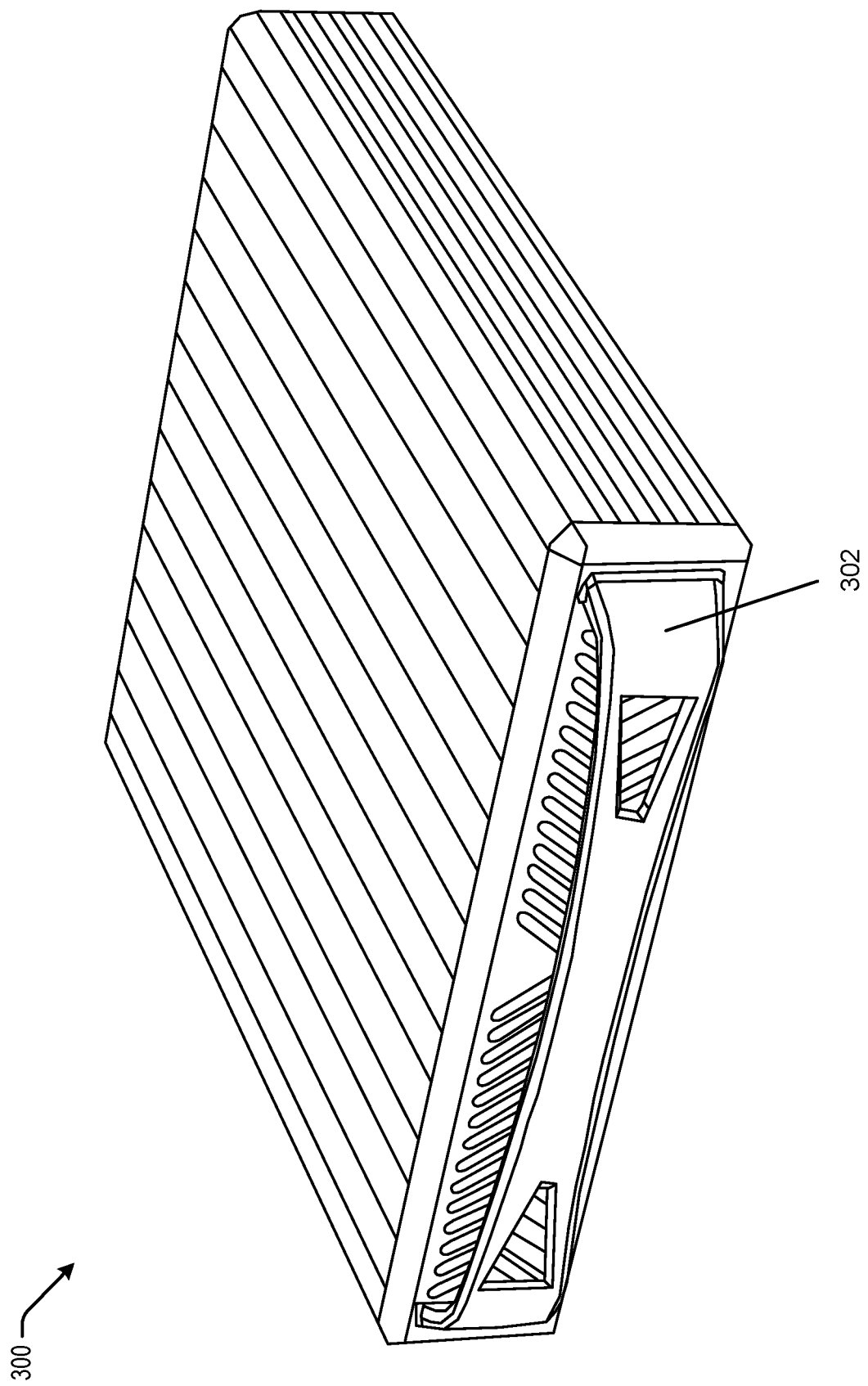
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure 300 may not be possible to open. However, in some cases, it might be possible, but it would require extreme measures.

Figure 4:
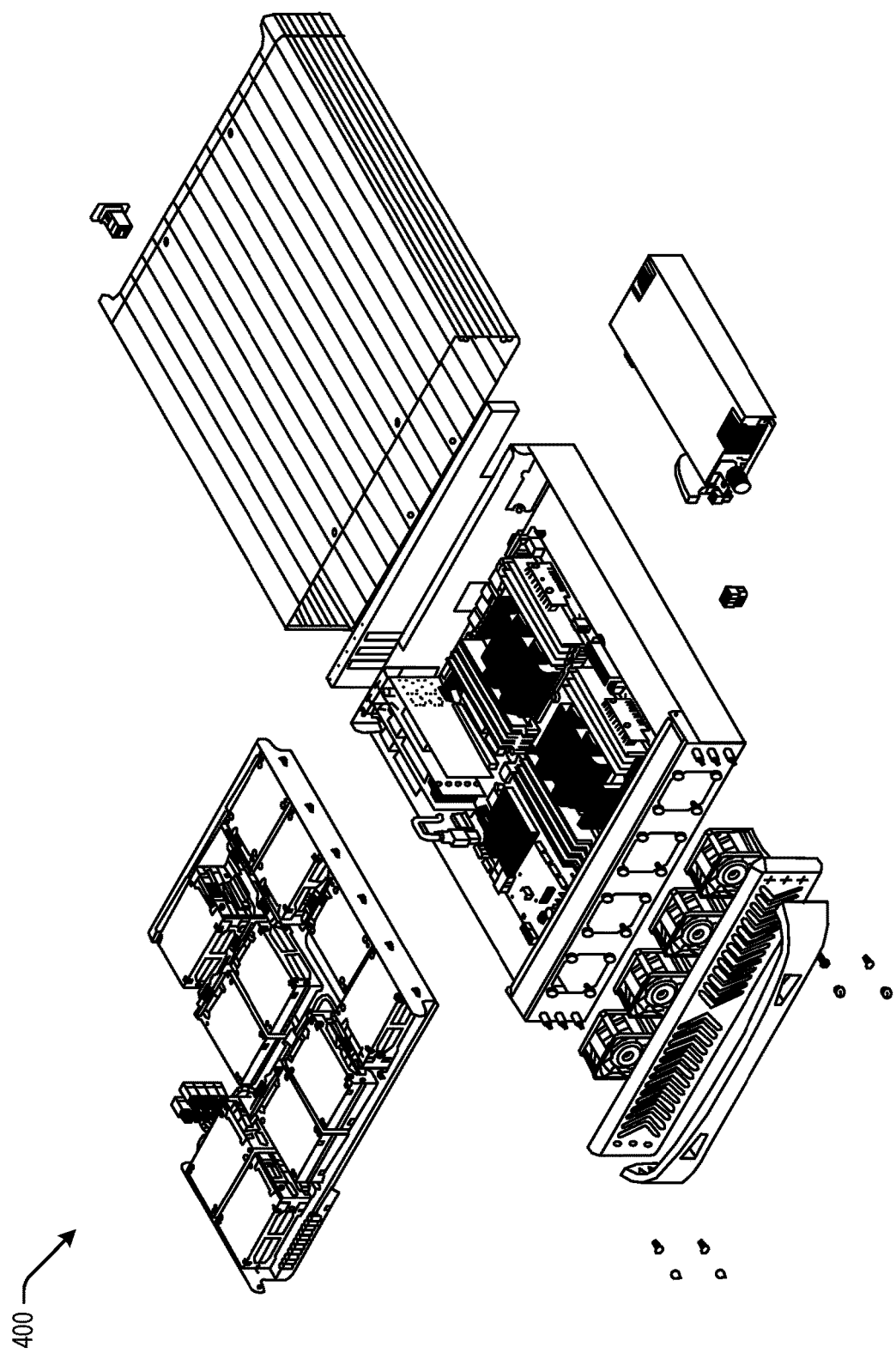
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
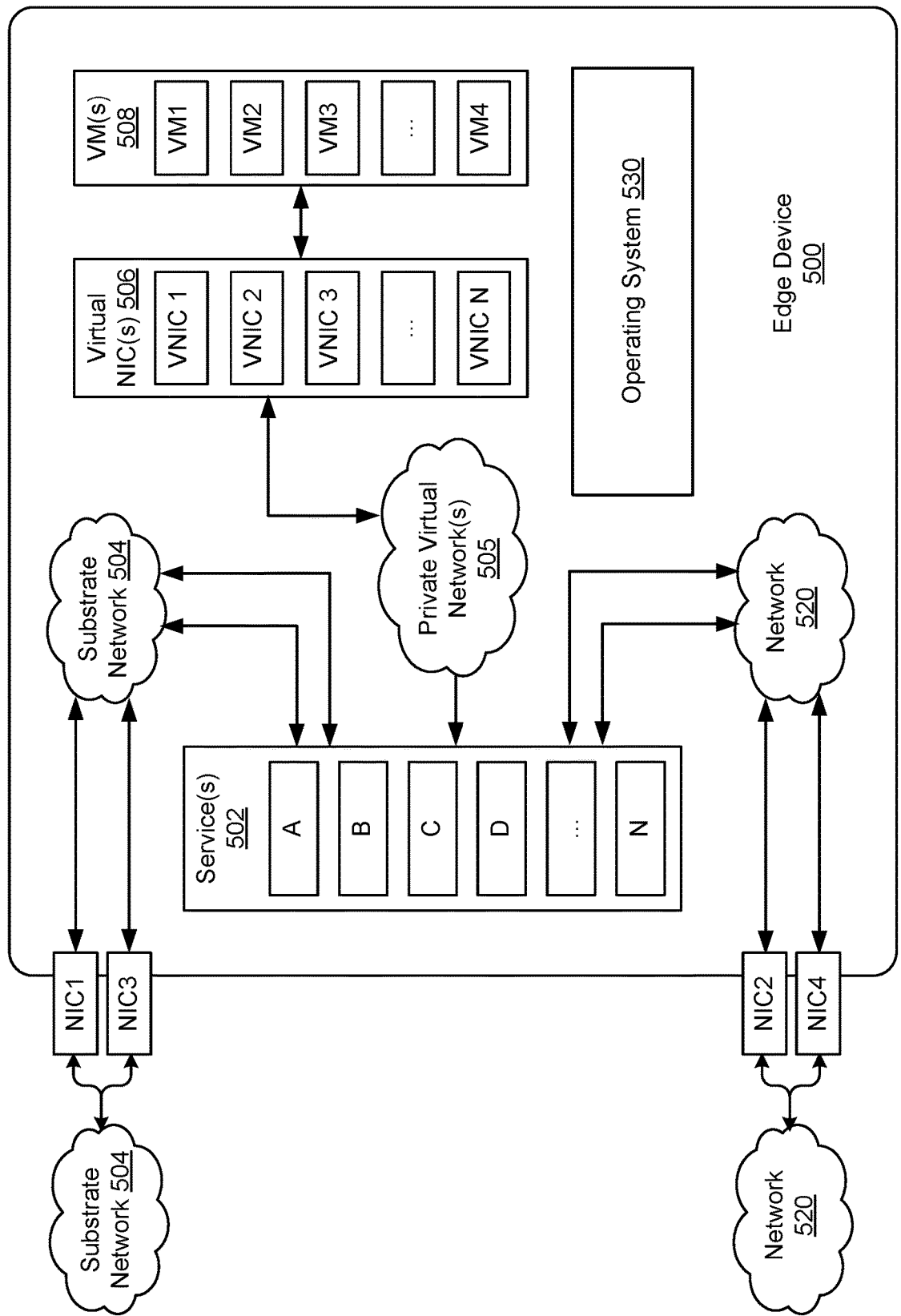
FIG. 5 is a block diagram of an example computer architecture of a cloud infrastructure edge computing device, according to at least one embodiment.

FIG. 5 is a block diagram of an example computer architecture of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations that may not be accessible by or have access to cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services, the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage or the like), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snapshots and copying block volumes. VM images and VM block volumes can be Ceph block devices. In some embodiments, the VM(s) implementing the distributed data storage platform will use system-reserved resources (e.g., eight CPU cores, or any subset of the total number of CPUs available on the edge device 500). For example in order to provision a boot volume, a block device image may be copied to a boot volume of the block device. The distributed data storage platform may use block devices that include multiple nodes for redundancy. If some node fails then the block device can continue to operate. In some embodiments, the distributed data storage platform (e.g., Ceph or the like), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snapshot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer. A "region" refers to a geographic location at which a service center resides. A "realm" refers to a logical collection of regions. Realms may be isolated from each other and do not share data.

In some embodiments, the edge device 500 may provide any suitable number of virtual networks (e.g., PVN(s) 505) using compute, memory, and networking resources (e.g., virtual network interface card(s) (VNIC(s) 506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 500, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
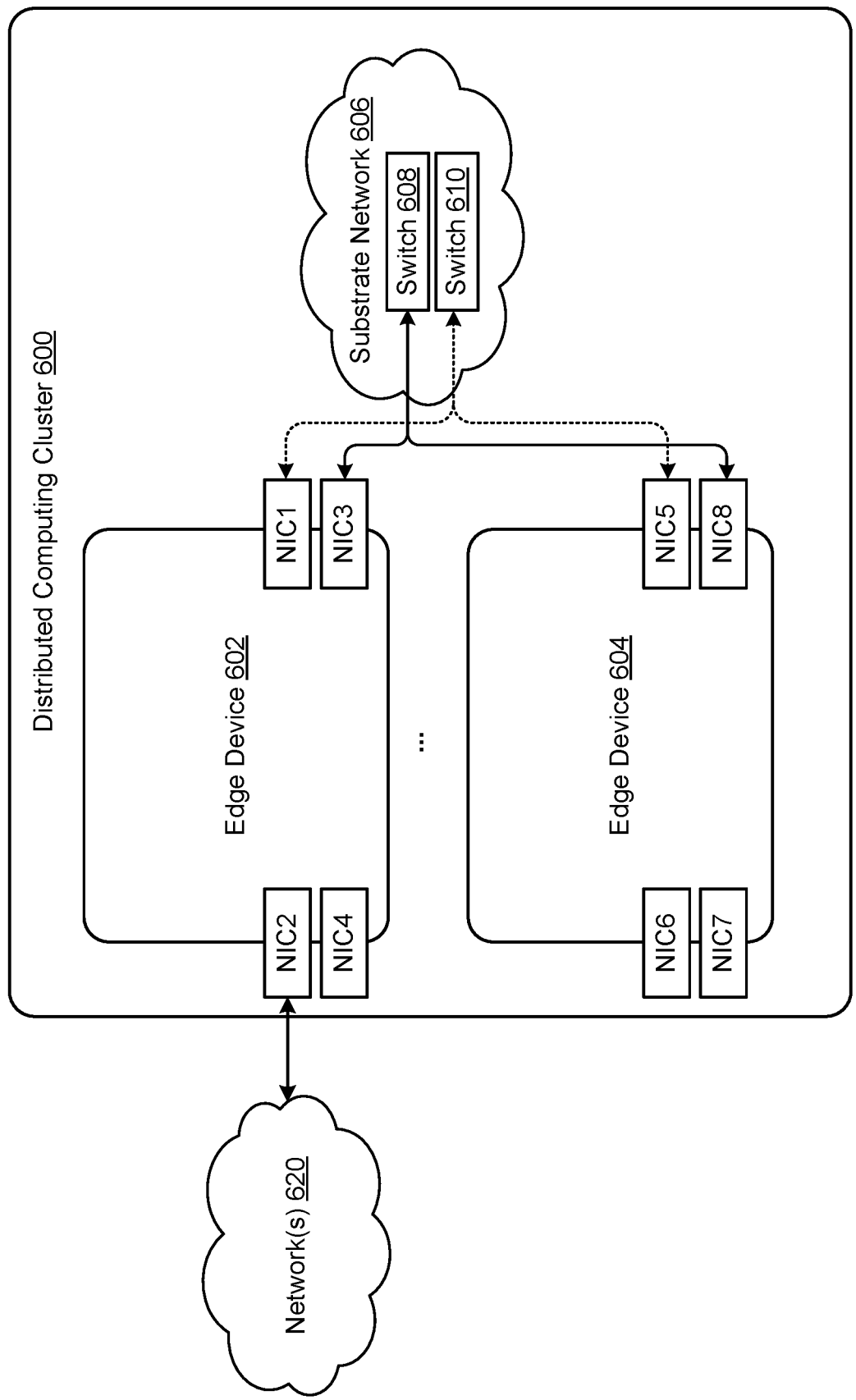
FIG. 6 is a block diagram depicting a distributed computing cluster that includes one or more edge computing devices, according to at least one embodiment.

FIG. 6 is a block diagram depicting a distributed computing cluster 600 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 600. In other embodiments, the user can configured the number and topology of the edge devices of the distributed computing cluster 600.

Figure 7:
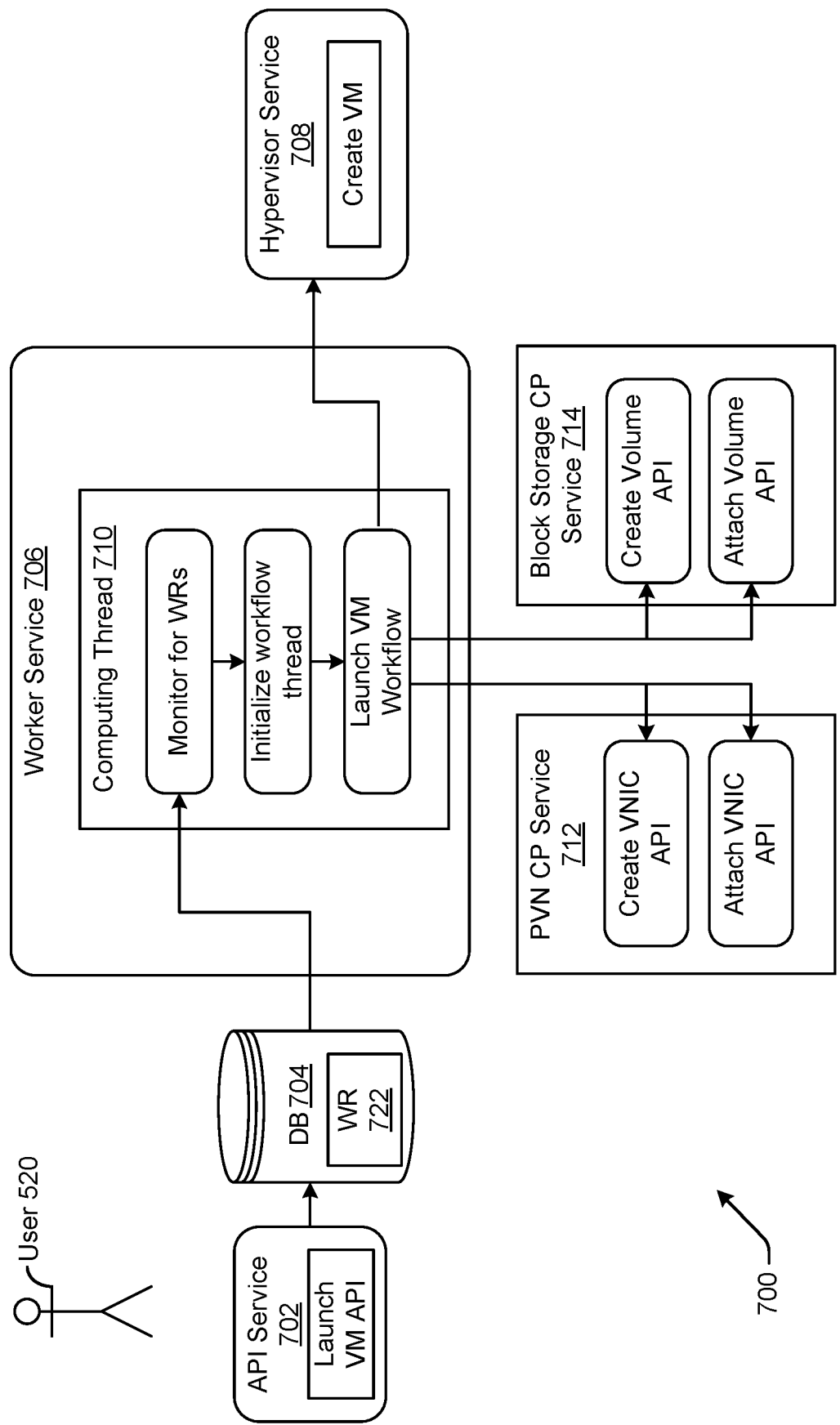
FIG. 7 is a block diagram depicting a flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database (DB) 704, worker service 706, hypervisor service 708, PVN CP service, Block storage CP service 714, although more or fewer services may be included. In some embodiments, each of the services of FIG. 7 are an example of a service of the service(s) 502 of FIG. 5. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device *202 of FIG. *2) to access a user interface with which he can make various selections indicating a desire to launch a VM. The user input may be received by the API service 702 (an example of the compute CP service of FIG. 5) which may generate a work request (WR) (e.g., WR 722) and utilize a predefined Launch VM API to store the work request in a distributed database (e.g., DB 704). In some embodiments, the DB 704 may be a computing cluster, which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Worker service 706 (e.g., an example of the compute CP service of FIG. 5) may be configured to execute one or more worker processes (e.g., one or more computing threads, such as computing thread 710). Some of these worker processes may be configured by the worker service 706 at any suitable time to execute a continuous and/or ongoing predefined workflow. By way of example, the worker service 706 may configure one or more worker threads (e.g., including computing thread 710) to monitor the DB 704 for new work requests (e.g., WR 722). The computing thread may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 504 of FIG. 5) to a workflow service (not depicted). The workflow service may be configured to identify, from one or more predefined workflows, a predefined workflow that corresponds to launching a VM, and therefore, to the WR 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data. In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

Figure 8:
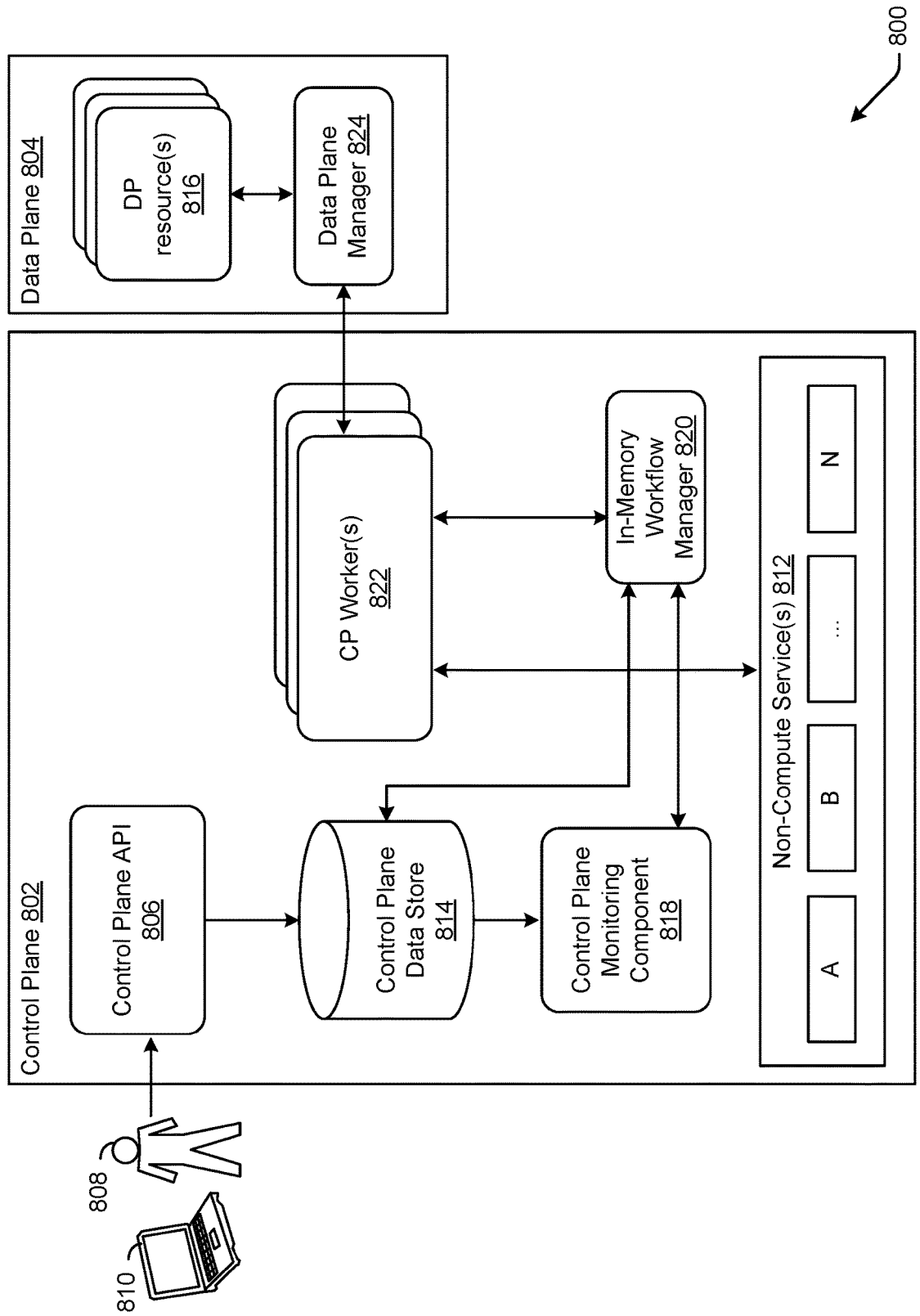
FIG. 8 is a block diagram depicting a hosting environment provided by an edge computing device, according to at least one embodiment.

FIG. 8 is a block diagram depicting a cloud-computing environment 800 provided by an edge computing device (an example of the edge devices of FIG. 1-6), according to at least one embodiment. Cloud-computing environment 800 may include control plane 802 and data plane 804.

In some embodiments, the control plane 802 may be responsible for accepting work requests that include intended state data that describes an intended state of a set of one or more data plane resources. For example, a work request may be received by control plane application programming interface (API) 806. The work request can be initiated by user 808 via a user device 810 interfacing with an edge computing device (not depicted) at which control plane 802 and data plane 804 operate. In some embodiments, control plane API 806 (e.g., an example of the API service 702 of FIG. 7) may be one of the service(s) 812 (an example of the service(s) 502 of FIG. 5). Control plane API 806 may be configured to receive any suitable number of work requests corresponding to one or more data resources (e.g., a virtual machine, a cluster of virtual machines, etc.) from the user device 810.

A work request may include a request identifier and intended state data. The request identifier may uniquely identify the work request such that the work request can be distinguishable from other work requests. By way of example, the request identifier for a particular work request can be an alphanumeric string of characters of any suitable length that is unique to that work request and with which that work request can be identified. Intended state data may include any suitable number of parameters. These parameters may define attributes of the data plane resource requested including, but not limited to, an identifier for the resource, an availability domain, a shape corresponding to the node, a number of processing units of the resource, an amount of random access memory (RAM) of the resource, an amount of disk memory, a role (e.g., a data node, a master node, etc.), a status (e.g., healthy), or the like. In some embodiments, the control plane API 806 may be configured to store all received work requests in a data store (e.g., a distributed data store) configured to store such information (e.g., control plane (CP) data store 814).

In some embodiments, CP data store 814 may be configured to store work requests and/or an intended state data corresponding to an intended state of the data plane 804. In some embodiments, the CP data store 814 may be configured to store a mapping of one or more data plane identifiers (DPIDs) of DP resource(s) 816 with intended state data and/or current state data. Intended state data refers to data that specifies one or more aspects of a DP resource which has been requested and to which the DP resource is intended to be modified. Current state data (sometimes referred to as "actual state data") corresponds to one or more parameters that identify one or more current aspects of a DP resource as currently operating.

The control plane 802 may include a control plane (CP) monitoring component 818. The CP monitoring component 818 may be configured to periodically (e.g., according to a predetermined frequency, schedule, etc.) determine whether the intended state data received by the control plane API 806 and stored in the CP data store 814 (e.g., from a previously received work request) matches current state data stored for a corresponding DP resource (if that DP resource currently exists). CP monitoring component 818 may be communicatively coupled to non-compute service(s) 812 (e.g., via substrate network 504 of FIG. 5) which may include any suitable number of cloud computing services configured to manage billing, identity, authorization, and the like. In some embodiments, CP monitoring component 818, in-memory workflow manager 820, and CP workers 822 are provided by a common service (e.g., worker service 706 of FIG. 7). Worker service 706 may be one of the service(s) 502 of FIG. 5. Non-compute service(s) 812 may be the remaining set of services of service(s) 502, excluding control plane API 806 and a service (e.g., worker service 706) that implements CP monitoring component 818, in-memory workflow manager 820, and CP workers 822. In some embodiments, CP monitoring component 818 is at least part of one of the service(s) 812. In some embodiments, CP monitoring component 818 may be communicatively coupled to in-memory workflow manager 820 and may be configured to invoke the functionality provided by the in-memory workflow manager 820. By way of example, if the CP monitoring component 818 determines that the current state data of a DP resource is not in line with (e.g., does not match) the intended state data stored in CP data store 814, CP monitoring component 818 may invoke the functionality of in-memory workflow manager 820 to rectify the discrepancy.

In some embodiments, in-memory workflow manager 820 may be configured to identify one or more predefined workflows which individually identify operations to perform to configure DP resource(s) 816 in accordance with corresponding intended state data. In some embodiments, the in-memory workflow manager 820 may be configured to initiate one or more workers of control plane (CP) worker(s) 822 and forward the workflow instructions and/or intended state data to a given CP worker to perform the operations related to configuring the corresponding DP resource(s) in accordance with the received intended state data. In some embodiments, the CP worker(s) 822 may provide service-specific orchestration operations. The CP worker(s) 822 may be communicatively coupled to any suitable number of services (e.g., service(s) 812) including any suitable combination of a compute service, a storage service, etc.). In some embodiments, the CP worker(s) 822 may be configured to provide instructions to data plane (DP) manager 824 for configuring one or more DP resources. DP manager 824 (e.g., an example of the hypervisor service 708 of FIG. 7) may be configured to create, modify, and/or remove or delete any suitable DP resource.

In some embodiments, DP manager 824 may be configured to manage any suitable number of computing components (e.g., the DP resource(s) 116 which may be, collectively, an example of a computing cluster). In some embodiments, the DP manager 824 may be configured to manage any suitable type of computing cluster (e.g., a Kubernetes cluster, a set of computing nodes used to execute containerized applications, etc.). The CP worker(s) 822 may be configured to execute any suitable operations to cause the DP manager 824 to execute any suitable orchestration operation on the DP resource(s) 816 in accordance with the instructions identified by in-memory workflow manager 820 to configure the DP resource(s) 816 in accordance with the intended state data. In some embodiments, CP monitoring component 818 may be communicatively coupled to DP resource(s) 816 and configured to monitor the health of DP resource(s) 816. In some embodiments, CP monitoring component 818 may be configured to transmit (e.g., to a user device of user 114 using any suitable form of electronic communication) any suitable health data indicating the health of one or more of the DP resource(s) 816. By way of example, CP monitoring component 818 may transmit any suitable health data via Control plane API 806 to user device 810. As another example, user device 810 may be configured to request (e.g., via CP API 806) and/or obtain current state data and/or heath data from the CP data store 814 periodically, or according to a predefined schedule.

In some embodiments, the CP monitoring component 818 may be configured to monitor and assess current state data of the DP resource(s) 816. In some embodiments, the CP monitoring component 818 may receive current state data store/update current state data of the DP resource(s) 816 within CP data store 814. Current state data may be provided by DP manager 824 to a corresponding CP worker, which in turn may provide the current state data to the in-memory workflow manager 820, which may then provide the current state data to the CP monitoring component 818. In some embodiments, CP worker(s) 822 and/or in-memory workflow manager 820 may update CP data store 814 directly with the current state data of any suitable DP resource such that the current state data of a given DP resource may be retrieved by the CP monitoring component 818 at any suitable time.

Although CP monitoring component 818, in-memory workflow manager 820, and CP worker(s) 822 are depicted as separate components of control plane 802, in some embodiments, any suitable combination of CP monitoring component 818, in-memory workflow manager 820, and/or CP worker(s) 822 may be provided by one service (e.g., worker service 706 of FIG. 7, an example of one of the services of service(s) 502 of FIG. 5).

Figure 9:
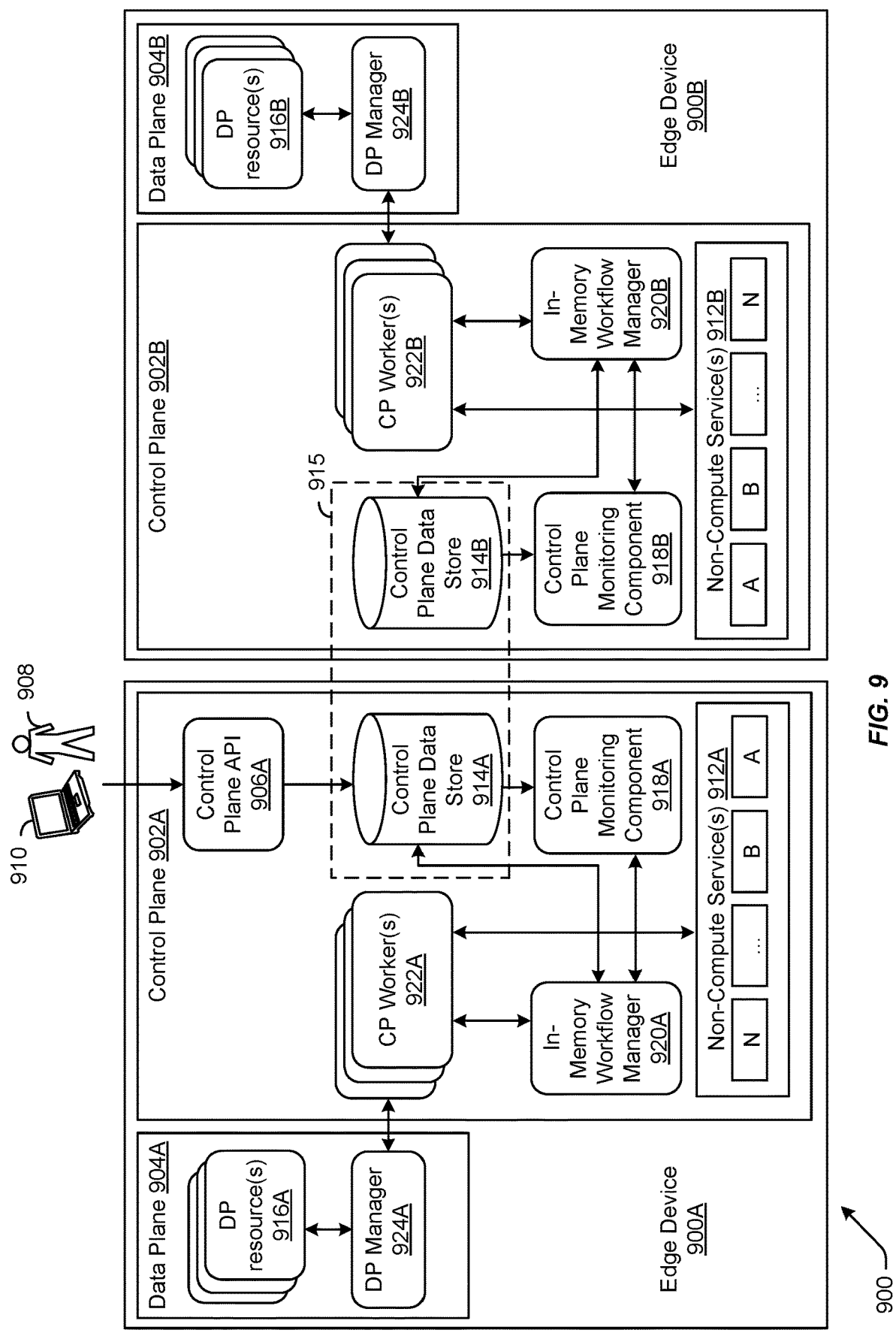
FIG. 9 is a block diagram depicting a number of hosting environments provided by a computing cluster including two edge computing devices, according to at least one embodiment.

FIG. 9 is a block diagram depicting a number of cloud-computing environments 900 provided by a computing cluster including two edge computing devices (e.g., edge devices 900A and 900B, each being an example of the edge devices of FIG. 1-6), according to at least one embodiment. Each cloud-computing environment may include a control plane and a data plane. By way of example, edge device 900A may include control plane 902A and data plane 904A. Edge device 900B may include control plane 902B and data plane 904B. In some embodiments, control plane 902A and 902B may operate as a distributed control plane and data plane 904A and 904B may operate as a distributed data plane.

The user device 910 may be configured to transmit work requests to edge device 900A. In some embodiments, the edge device 900A may be the sole edge device to include a public network interface (e.g., NIC2 and/or NIC 4 of FIG. 5) through which user device 910 may transmit work requests and receive status on previously transmitted work requests. Thus, in some embodiments, edge device 900A alone may be configured to receive data from a public network (e.g., network 520) through which user device 910 and edge device 900A may be communicatively connected.

In some embodiments, the control plane 902A may be responsible for accepting work requests that include intended state data that describes an intended state of a set of one or more data plane resources. For example, a work request may be received by control plane application programming interface (API) 906A. The work request can be initiated by user 908 via user device 910 interfacing with control plane 902A. In some embodiments, control plane API 906A (e.g., an example of the API service 702 of FIG. 7) may be one of the service(s) 912A (an example of the service(s) 502 of FIG. 5). Control plane API 906A may be configured to receive any suitable number of work requests corresponding to one or more data resources (e.g., a virtual machine, a cluster of virtual machines, etc.) from the user device 910.

In some embodiments, the control plane API 906A may be configured to store received work requests with CP data store 914A. In some embodiments, CP data store 914A and 914B (collectively referred to as "CP data store 914) form a distributed storage which is accessible to the edge devices 900A and 900B. As described above, these work requests may include a request identifier and intended state data corresponding to an intended state of the data plane 904A and 904B, which may operate as a distributed data plane (referred to as "data plane 904). In some embodiments, the CP data store 915 may be configured to store a mapping of one or more data plane identifiers (DPIDs) of DP resource(s) 916A and 916B with intended state data and/or current state data.

Each edge device may include a corresponding (CP) monitoring service within its corresponding control plane. By way of example, the edge device 900A may include CP monitoring service 918A and edge device 900B may include CP monitoring service 918B. The CP monitoring services 918A and 918B may individually be a service that is configured to periodically (e.g., according to a predetermined frequency, schedule, etc.) determine whether the intended state data received by the control plane API 906A and stored in the CP data store 915 (e.g., from a previously received work request) matches current state data stored for a corresponding DP resource (if that DP resource currently exists). Each of the CP monitoring services 918A and 918B may be communicatively coupled to corresponding service(s) 912A and 912B (e.g., via substrate network 504 of FIG. 5), respectively. Service(s) 912A and 912B may include any suitable number of cloud computing services configured to manage billing, identity, authorization, and the like. In some embodiments, CP monitoring services 918A and/or 918B is one of the service(s) 912A and/or 912B, respectively. In some embodiments, the CP monitoring service of each edge device may be communicatively coupled to a corresponding in-memory workflow manager (e.g., in-memory workflow manager 920A and 920B, respectively) and may be configured to invoke the functionality provided by the corresponding in-memory workflow manager. By way of example, if the CP monitoring service 918A or 918B determines that the current state data of a DP resource is not in line with (e.g., does not match) the intended state data stored in CP data store 914, that CP monitoring service may invoke the functionality of the corresponding in-memory workflow manager to rectify the discrepancy.

In some embodiments, in-memory workflow managers 920A and 920B may be individually configured to identify one or more predefined workflows which individually identify operations to perform to configure DP resource(s) 916A and 916B, respectively, in accordance with corresponding intended state data. In some embodiments, the in-memory workflow manager 920A may be configured to initiate one or more workers of control plane (CP) worker(s) 922A and forward the workflow instructions and/or intended state data to a given CP worker to perform the operations related to configuring the corresponding DP resource(s) 916A in accordance with the received intended state data. Similarly, the in-memory workflow manager 920B may be configured to initiate one or more workers of control plane (CP) worker(s) 922B and forward the workflow instructions and/or intended state data to a given CP worker to perform the operations related to configuring the corresponding DP resource(s) 916B in accordance with the received intended state data. In some embodiments, the CP worker(s) 922A and/or 922B may provide service-specific orchestration operations. The CP worker(s) 922A and/or 922B may be communicatively coupled to any suitable number of services (e.g., service(s) 912A and 912B, respectively) including any suitable combination of a compute service, a storage service, etc.). In some embodiments, the CP worker(s) 922A and/or 922B may be configured to provide instructions to data plane (DP) manager 924A or DP manager 924B, respectively, for configuring one or more DP resources. DP manager 924A and/or 924B may each be an example of the hypervisor service 708 of FIG. 7 and may each be configured to create, modify, and/or remove or delete any suitable DP resource.

In some embodiments, DP manager 924A and 924B may be configured to manage any suitable number of computing components (e.g., the DP resource(s) 916A and 916B, respectively which may be, collectively, an example of a computing cluster). In some embodiments, the DP manager 924A and/or 924B may be configured to manage any suitable type of computing cluster (e.g., a Kubernetes cluster, a set of computing nodes used to execute containerized applications, etc.). The CP worker(s) 922A and/or 922B may be configured to execute any suitable operations to cause the corresponding DP manager to execute any suitable orchestration operation on the corresponding DP resource(s) in accordance with the instructions identified by the corresponding in-memory workflow manager to configure the corresponding DP resource(s) in accordance with the intended state data. In some embodiments, CP monitoring services 918A and 918B may be communicatively coupled to corresponding DP resource(s) 916A and 916B, respectively, and may be configured to monitor the health of those corresponding DP resource(s). In some embodiments, CP monitoring service 918A and/or 918B may be configured to transmit (e.g., to a user device of user 908 using any suitable form of electronic communication) any suitable health data indicating the health of one or more of the DP resource(s) 916A and/or 916B. By way of example, CP monitoring service 918A may transmit any suitable health data via Control Plane API 906A to user device 910. As another example, user device 810 may be configured to request (e.g., via CP API 906A) and/or obtain current state data and/or heath data from the CP data store 915 periodically, or according to a predefined schedule.

The CP workers may be configured to instruct any suitable DP manager, regardless of whether the DP manager resides at the same edge device. By way of example, CP worker(s) 922A may be configured to instruct DP manager 924B to create, modify, and/or delete/remove any suitable number of DP resource(s) 916B. Likewise, CP worker(s) 922B may be configured to instruct DP manager 924A to create, modify, and/or delete/remove any suitable number of DP resource(s) 916A. In some embodiments, CP monitoring service 918A may be configured to store health data within CP data store 914A and CP monitoring service 918B may be configured to store health data within CP data store 914B. In some embodiments, control plane API 906A may poll for current status of DP resource(s) 916A and/or 916B (collectively, referred to as "DP resource(s) 916) from CP data store 914. Thus, the health data and/or current state data of any given DP resource may be obtained (e.g., using the control plane API 906A) by the user device 910 via the public network interface between edge device 900A and user device 910. In some embodiments, the user device 910 may poll for/request current state data periodically (e.g., every 1-2 seconds after submitting a work request).

In some embodiments, the CP monitoring services 918A and 918B may each be configured to monitor and assess current state data of the DP resource(s) 916A and 916B, respectively. In some embodiments, each CP monitoring service may receive current state data store/update current state data of the corresponding DP resource(s) within CP data store 814. Current state data may be provided by DP manager 924A or 924B to a corresponding CP worker, which in turn may provide the current state data to the in-memory workflow manager 920A or 920B, which may then provide the current state data to the CP monitoring service 918A or 918B. In some embodiments, CP worker(s) 922A and/or 922B and/or in-memory workflow manager 920A and/or 920B may update CP data store 814 directly with the current state data of any suitable DP resource such that the current state data of a given DP resource may be retrieved by the CP monitoring service 918A or 918B at any suitable time.

Figure 10:
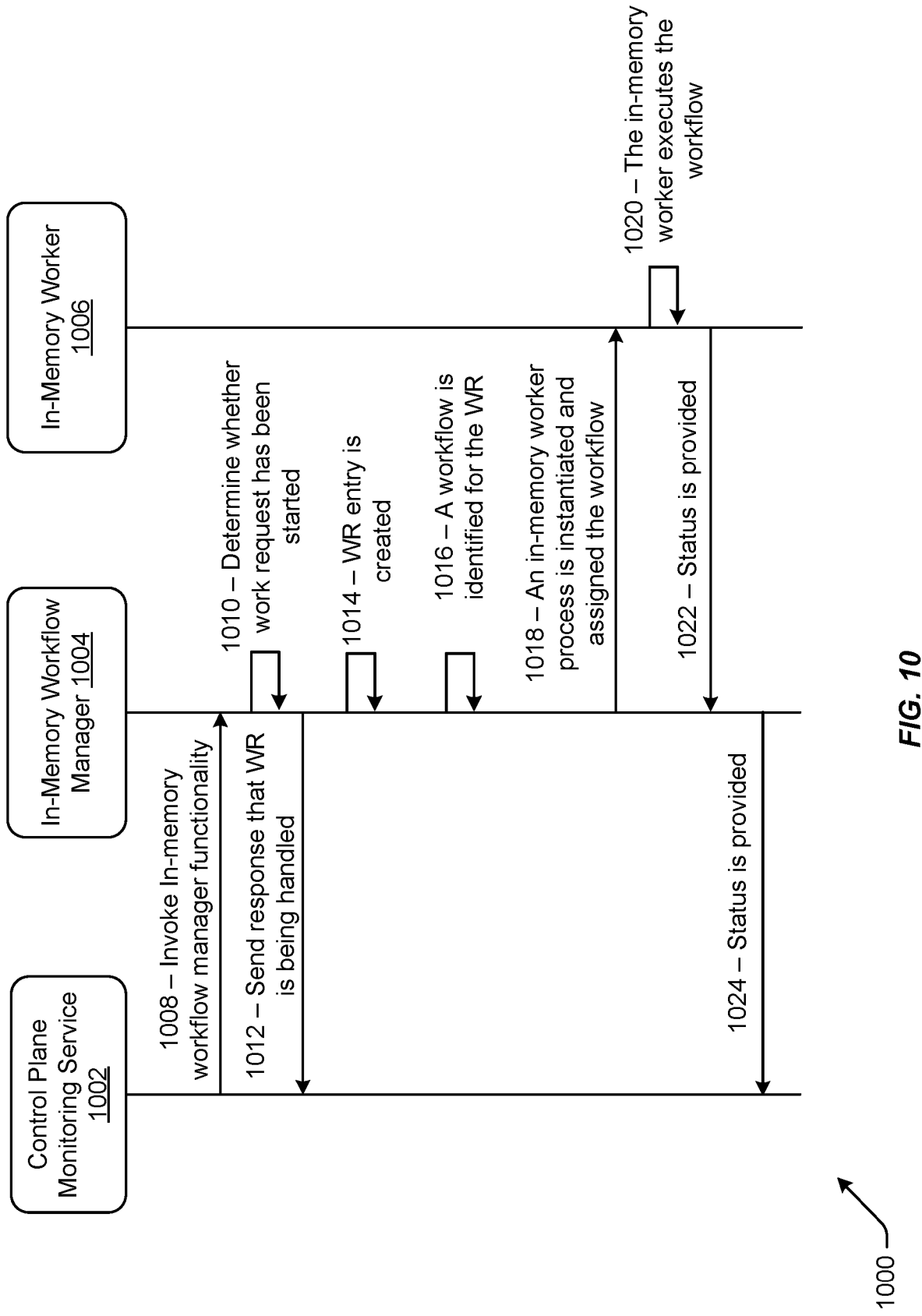
FIG. 10 illustrates an example flow for performing one or more operations in connection with a work request, in accordance with at least one embodiment.

FIG. 10 illustrates an example flow 1000 for performing one or more operations in connection with a work request, in accordance with at least one embodiment. The flow 1000 may be performed by control plane (CP) monitoring service 1002 (e.g., an example of the CP monitoring services 918A and/or 918B of FIG. 9, CP monitoring component 818 of FIG. 8, etc.), in-memory workflow manager 1004 (e.g., an example of the in-memory workflow manager 920A and/or 920B of FIG. 9, in-memory workflow manager 820 of FIG. 8, etc.), and in-memory worker 1006 (e.g., an example of the CP worker(s) 922A and/or 922B of FIG. 9, CP worker(s) 822 of FIG. 8, etc.). In some embodiments, any suitable combination of the CP monitoring service 1002, the in-memory workflow manager 1004, and the in-memory worker 1006 may be provided by a common service (e.g., one of the service(s) 502 of FIG. 5).

The flow 1000 may begin at 1008, where the CP monitoring service 1002 may invoke (e.g., via function call) the functionality of in-memory workflow manager 1004. The call performed at 1008 may include a request identifier for the work request. The call performed at 1008 may be executed in response to the CP monitoring service 1002 identifying that the current state data for a given DP resource does not match the intended state data for that resource.

At 1010, in-memory workflow manager 1004 my determine, from a portion of a data store (e.g., a portion of the CP data store 915 of FIG. 9, a portion of CP data store 814 of FIG. 8, etc.) whether another component has begun executing operations corresponding to the work request. By way of example, the in-memory workflow manager 1004 may check within a portion of the data store that is dedicated to storing request identifiers corresponding to work requests that a control plane worker has commenced processing. If the in-memory workflow manager 1004 checks the dedicated portion of the data store and the request identifier has already been stored in that dedicated portion of the data store, then the in-memory workflow manager 1004 may determine that the request is already being (or has already been) handled by another computing component (e.g., another in-memory workflow manager of another edge device) and in-memory workflow manager 1004 may send a response at 1012 to CP monitoring service 1002 that indicates the request is being handled (or has been handled) by another computing component. Alternatively, the in-memory workflow manager 1004 may determine that the request identifier has not been stored in the dedicated portion of the data store. In this scenario, the in-memory workflow manager 1004 may determine that the request has not yet been handled. If so, the flow 1000 may proceed to 1014.

At 1014, the in-memory workflow manager 1004 may create an entry for the work request within the dedicated portion of the data store. In some embodiments, the request identifier may be stored within the dedicated portion of the data store to indicate that a computing component (e.g., in-memory workflow manager 1004) has commenced processing the request. In some embodiments, the dedicated portion of the data store (e.g., a distributed data store such as the CP data store 915 of FIG. 9, the CP data store 814 of FIG. 8, etc.) may be accessible to any suitable in-memory workflow manager operating at any suitable edge device of a computing cluster. By storing the request identifier within the dedicated portion of the data store, in-memory workflow manager 1004 ensures that it is the only computing component to process the work request. In this manner, in-memory workflow manager 1004 can ensure that duplicate processing of the request by another computing component is avoided.

At 1016, the in-memory workflow manager 1004 may identify one or more predefined workflows for configuring one or more data plane resource (e.g., one or more virtual machines) to be in accordance with the intended state data corresponding to the request identifier (as retrieved from the data store).

At 1018, the in-memory workflow manager 1004 may instantiate in-memory worker 1006 (e.g., an example of an execution thread). In-memory workflow manager 1004 may provide the one or more workflows to the in-memory worker 1006 for execution.

At 1020, in-memory worker 1006 may execute any suitable operations corresponding to the one or more workflows identified by the in-memory workflow manager 1004.

At 1022, and once the operations performed at 1020 are complete, the in-memory worker 1006 may provide status of the workflow to in-memory workflow manager 1004. In some embodiments, the status may include current state data indicating parameters which specify a current state of the DP resource(s) affected by the work request.

At 1024, the in-memory workflow manager 1004 may forward the status of the DP resource(s) to the CP monitoring service 1002. Alternatively, the in-memory worker 1006 and/or the in-memory workflow manager 1004 may store the status and/or current state data within a data store accessible to the CP monitoring service 1002, such as the CP data stores 814 and/or 914 of FIGS. 8 and 9, respectively.

Figure 11:
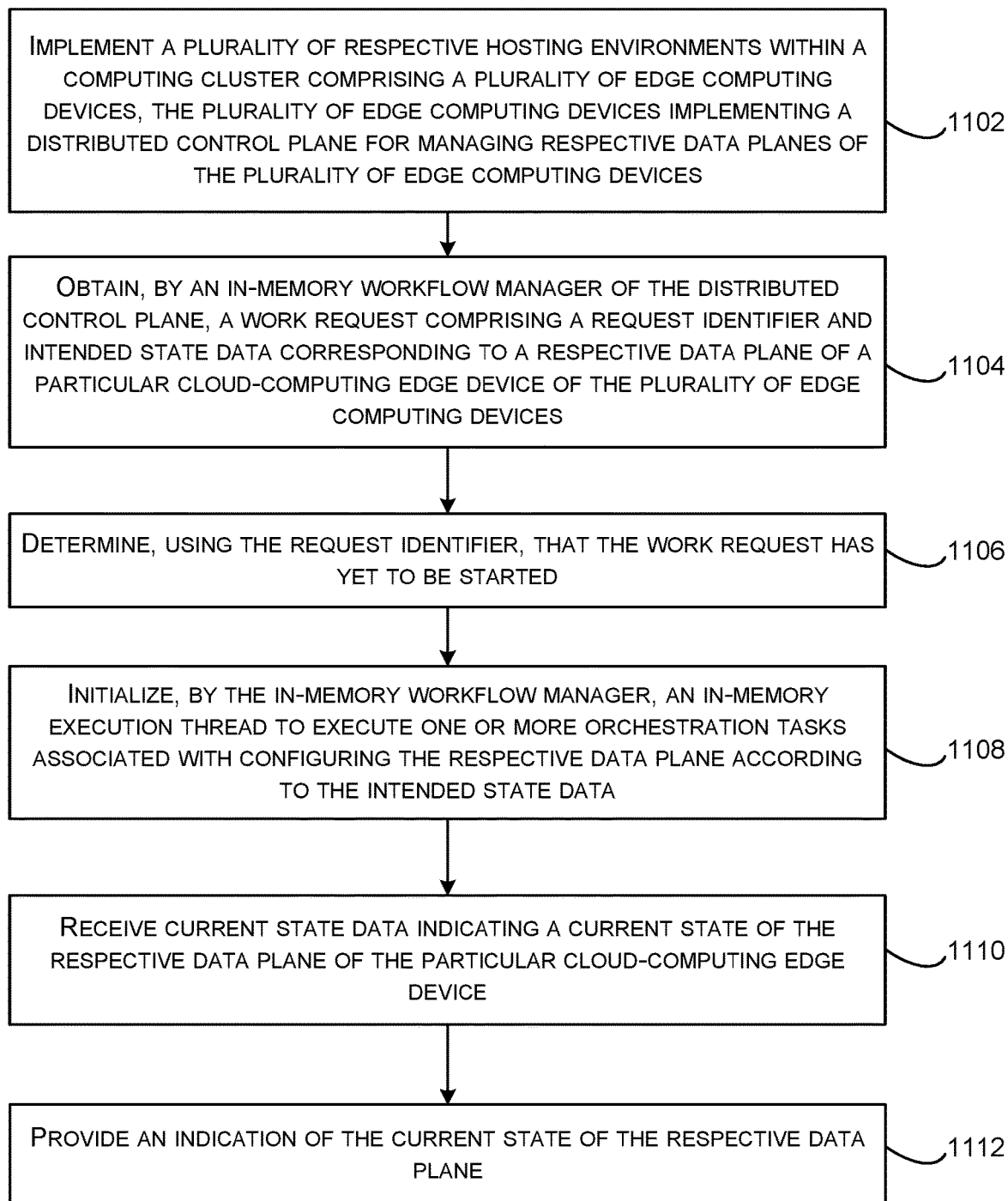
FIG. 11 is a block diagram illustrating an example method for providing in-memory workflow management at an edge computing device, in accordance with at least one embodiment.

FIG. 11 is a block diagram illustrating an example method 1100 for providing in-memory workflow management at an edge computing device, in accordance with at least one embodiment. The method 1100 may be performed by any suitable number of edge devices (e.g., the edge devices 900A and 900B of FIG. 9). In some embodiments, the method 1100 may include more or fewer steps than the number depicted in FIG. 11. It should be appreciated that the steps of method 1100 may be performed in any suitable order.

The method 1100 may begin at 1102, where a plurality of respective hosting environments (e.g., data planes 904A and 904B of FIG. 9) may be implemented within a computing cluster comprising a plurality of edge computing devices (e.g., the edge devices 900A and 900B). In some embodiments, the plurality of edge computing devices implement a distributed control plane (e.g., collectively, control planes 902A and 902B) for managing respective data planes (e.g., data planes 904A and 904B) of the plurality of edge computing devices.

At 1104, a work request may be obtained by an in-memory workflow manager of the distributed control plane. By way of example, in-memory workflow manager 920B may obtain a work request. In some embodiments, the work request may comprise a request identifier and intended state data corresponding to a respective data plane of a particular cloud-computing edge device of the plurality of edge computing devices. For example, the work request may include intended state data corresponding to a DP resource(s) 916B of data plane 904B of FIG. 9.

At 1106, using the request identifier, it may be determined that the work request has yet to be started. By way of example, the in-memory workflow manager 920B may identify that the request identifier has not yet been stored in a dedicated portion of CP data store 915 of FIG. 9. As a result, the in-memory workflow manager 920B may determine that the work request has not yet been processed by a computing component (e.g., the in-memory workflow manager 920B itself, or any suitable computing component of the edge device cluster comprising edge devices 900A and 900B).

At 1108, the in-memory workflow manager 920B may initialize an in-memory execution thread (e.g., one of CP worker(s) 922B of FIG. 9) to execute one or more orchestration tasks associated with configuring the respective data plane according to the intended state data. By way of example, the in-memory workflow manager 920B may instantiate the in-memory execution thread (e.g., one of the CP worker(s) 922B of FIG. 9) and pass one or more instructions that indicate the in-memory execution thread is to execute the one or more orchestration tasks. The in-memory execution thread may be configured to instruct a DP manager (e.g., DP manager 924B of FIG. 9, an example of the hypervisor service 708 of FIG. 7) to perform one or more operations to configure one or more of the DP resource(s) 916B in accordance with the intended state data.

At 1110, current state data indicating a current state of the respective data plane of the particular cloud-computing edge device may be received. The current state data may be stored (e.g., in CP data store 915).

At 1112, an indication of the current state of the respective data plane may be provided (e.g., to the user device 910). By way of example, in some embodiments, the current state data may be retrieved (e.g., by the user device 910 using the control plane API 906A) and provided to the user device 910 of FIG. 9. Subsequently, the user device 910 may present the current state data.

Although the example above includes modifying DP resource(s) of an edge device by an in-memory workflow manager operating at that edge device, embodiments include using an in-memory workflow manager and/or CP worker(s) to instruct a DP manager of another edge device to modify the DP resources of that other edge device. Thus, any in-memory workflow manager of any suitable edge device may be utilized to perform modifications to any suitable data plane of any suitable edge device in an edge device cluster.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
    implementing, by an edge computing device of a plurality of edge computing devices of a computing cluster, a hosting environment comprising at least part of a distributed control plane implemented by the plurality of edge computing devices, the distributed control plane being configured to manage respective data planes of the plurality of edge computing devices;
    obtaining, by a computing component of the distributed control plane executed by the edge computing device, a work request comprising intended state data corresponding to a respective data plane of a particular cloud-computing edge device of the plurality of edge computing devices;
    executing, by the computing component, operations to cause one or more orchestration tasks to be executed, the one or more orchestration tasks being associated with configuring the respective data plane according to the intended state data;
    obtaining, by the computing component, current state data indicating a current state of the respective data plane of the particular cloud-computing edge device; and
    providing, by the computing component, an indication of the current state of the respective data plane.

2. The computer-implemented method of claim 1, wherein the work request is initiated by from a user device configured to communicate with one edge computing device of the plurality of edge computing devices.

3. The computer-implemented method of claim 1, wherein the computing component is an in-memory workflow manager provided by a container executing on the edge computing device.

4. The computer-implemented method of claim 1, wherein the one or more orchestration tasks associated with configuring the respective data plane according to the intended state data are executed in response to:
    obtaining, from a distributed data store accessible to the plurality of edge computing devices, historical state data indicating respective current states of the respective data plane of the particular cloud-computing edge device;
    comparing the historical state data and the intended state data; and
    determining that there is a difference between the historical state data and the intended state data obtained from the distributed data store.

5. The computer-implemented method of claim 1, wherein the work request further comprises a request identifier, and wherein the computer-implemented method further comprises determining, by the computing component that the work request has yet to be started based at least in part on determining that a record associated with the request identifier is not yet stored in a distributed data store accessible to the plurality of edge computing devices.

6. The computer-implemented method of claim 1, wherein the plurality of edge computing devices are communicatively coupled with one another via a substrate network that is different from a public network.

7. The computer-implemented method of claim 1, wherein the computing component executing on the edge computing device identifies the one or more orchestration tasks associated with configuring the respective data plane according to the intended state data.

8. An edge computing device operating as part of a computing cluster of a plurality of edge computing devices, the edge computing device comprising:
    one or more processors; and
    one or more memories configured with computer-executable instructions that, when executed by the one or more processors, cause the edge computing device to:
    implement a hosting environment within the computing cluster, the hosting environment comprising at least part of a distributed control plane implemented by the plurality of edge computing devices, the distributed control plane being configured to manage respective data planes of the plurality of edge computing devices;
    obtain, by a computing component of a portion of the distributed control plane executed by the edge computing device, a work request comprising intended state data corresponding to a respective data plane of the edge computing device;
    initialize, by the computing component, operations to cause one or more orchestration tasks to be executed, the one or more orchestration tasks being associated with configuring the respective data plane according to the intended state data;
    receive current state data indicating a current state of the respective data plane of the edge computing device; and
    provide an indication of the current state of the respective data plane.

9. The edge computing device of claim 8, wherein the work request is initiated by a user device configured to communicate with one edge computing device of the plurality of edge computing devices.

10. The edge computing device of claim 8, wherein the computing component is an in-memory workflow manager provided by a container executing on the edge computing device.

11. The edge computing device of claim 8, wherein the one or more orchestration tasks associated with configuring the respective data plane according to the intended state data are executed in response to:
    obtaining, from a distributed data store accessible to the plurality of edge computing devices, historical state data indicating respective current states of the respective data plane of the edge computing device;
    comparing the historical state data and the intended state data; and
    determining that there is a difference between the historical state data and the intended state data obtained from the distributed data store.

12. The edge computing device of claim 8, wherein the work request further comprises a request identifier, and wherein executing the computer-executable instructions further causes the edge computing device to determine that the work request has yet to be started based at least in part on determining that a record associated with the request identifier is not yet stored in a distributed data store accessible to the plurality of edge computing devices.

13. The edge computing device of claim 8, wherein the plurality of edge computing devices are communicatively coupled with one another via a substrate network that is different from a public network.

14. The edge computing device of claim 8, wherein the computing component executing on the edge computing device identifies the one or more orchestration tasks associated with configuring the respective data plane according to the intended state data.

15. A non-transitory computer-readable storage medium comprising computer-executable instructions that, when executed with one or more processors of an edge computing device, cause the edge computing device to:
- implement a hosting environment within a computing cluster comprising a plurality of edge computing devices, the hosting environment comprising at least part of a distributed control plane implemented by the plurality of edge computing devices, the distributed control plane being configured to manage respective data planes of the plurality of edge computing devices;
- obtain, by a computing component of a portion of the distributed control plane executed by the edge computing device, a work request comprising intended state data corresponding to a respective data plane of the edge computing device;
- initialize, by the computing component, operations to cause one or more orchestration tasks to be executed, the one or more orchestration tasks being associated with configuring the respective data plane according to the intended state data;
- receive current state data indicating a current state of the respective data plane of the edge computing device; and
- provide an indication of the current state of the respective data plane.

16. The non-transitory computer-readable storage medium of claim 15, wherein the computing component is an in-memory workflow manager provided by a container executing on the edge computing device.

17. The non-transitory computer-readable storage medium of claim 15, wherein the one or more orchestration tasks associated with configuring the respective data plane according to the intended state data are executed in response to:
- obtaining, from a distributed data store accessible to the plurality of edge computing devices, historical state data indicating respective current states of the respective data plane of the edge computing device;
- comparing the historical state data and the intended state data; and
- determining that there is a difference between the historical state data and the intended state data obtained from the distributed data store.

18. The non-transitory computer-readable storage medium of claim 15, wherein the work request further comprises a request identifier, and wherein executing the computer-executable instructions further causes the edge computing device to determine that the work request has yet to be started based at least in part on determining that a record associated with the request identifier is not yet stored in a distributed data store accessible to the plurality of edge computing devices.

19. The non-transitory computer-readable storage medium of claim 15, wherein the plurality of edge computing devices are communicatively coupled with one another via a substrate network that is different from a public network.

20. The non-transitory computer-readable storage medium of claim 15, the computing component executing on the edge computing device identifies the one or more orchestration tasks associated with configuring the respective data plane according to the intended state data.

* * * * *

UNITED STATES PATENT AND TRADEMARK OFFICE
CERTIFICATE OF CORRECTION

PATENT NO. : 11,936,521 B2
APPLICATION NO. : 18/296348
DATED : March 19, 2024
INVENTOR(S) : Maheshwari et al.

It is certified that error appears in the above-identified patent and that said Letters Patent is hereby corrected as shown below:

In the Specification

In Column 3, Line 19, delete "device" and insert -- device) --, therefor.

In Column 4, Line 16, delete "center" and insert -- center) --, therefor.

In Column 9, Line 3, delete "compute" and insert -- computer --, therefor.

In Column 9, Line 50, delete "service)." and insert -- service. --, therefor.

In Column 9, Line 66, delete "(RBD)" and insert -- (RBD)) --, therefor.

In Column 11, Line 40, delete "FIG. 5." and insert -- FIG. 5.) --, therefor.

In Column 13, Line 65, delete "FIG." and insert -- FIGS. --, therefor.

In Column 16, Line 26, delete "FIG." and insert -- FIGS. --, therefor.

In Column 17, Line 64, delete "etc.)" and insert -- etc. --, therefor.

In Column 19, Line 33, delete "my" and insert -- may --, therefor.

In the Claim

In Column 26, Line 33, in Claim 20, after "15," insert -- wherein --, therefor.

Signed and Sealed this
Twenty-third Day of July, 2024

Katherine Kelly Vidal
*Director of the United States Patent and Trademark Office*